United States Patent [19]

Rohr et al.

[11] 4,221,581

[45] Sep. 9, 1980

[54] PHENOXYPHENOXYALKANECARBOXYLIC ACID ESTERS

[75] Inventors: Otto Rohr, Therwil, Switzerland; Georg Pissiotas, Lörrach, Fed. Rep. of Germany; Beat Böhner, Binningen, Switzerland

[73] Assignee: Ciba-Geigy Corporation, Ardsley, N.Y.

[21] Appl. No.: 953,236

[22] Filed: Oct. 20, 1978

[30] Foreign Application Priority Data

Oct. 25, 1977 [CH] Switzerland ............... 12961/77

[51] Int. Cl.² .................. A01N 9/12; A01N 9/24; A01N 9/20
[52] U.S. Cl. .................. 71/70; 260/455 R; 260/465 D; 560/21; 71/100; 71/108; 71/109; 71/76; 71/72; 71/105
[58] Field of Search .............. 260/455 R, 465 D; 560/21; 71/100, 108, 109, 76, 72, 70, 105

[56] References Cited

U.S. PATENT DOCUMENTS

| | | | |
|---|---|---|---|
| 3,784,635 | 1/1974 | Theissen | 560/21 |
| 4,106,925 | 8/1978 | Rohr et al. | 260/455 R |
| 4,134,753 | 1/1979 | Horlein et al. | 560/21 |

Primary Examiner—Henry R. Jiles
Assistant Examiner—Robert C. Whittenbaugh
Attorney, Agent, or Firm—Harry Falber

[57] ABSTRACT

The present invention relates to novel herbicidally active phenoxyphenoxyalkanecarboxylic acid esters, compositions which contain these compounds as active ingredient, and a method of selectively controlling weeds in crops of cultivated plants or of regulating plant growth which comprises the use of these compounds.

The phenoxyphenoxyalkanecarboxylic acid esters have the formula

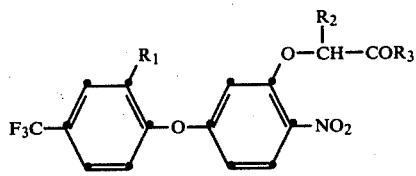

wherein
$R_1$ is hydrogen, halogen or cyano,
$R_2$ is hydrogen or lower alkyl,
$R_3$ is a radical $OR_4$ or $SR_5$,
$R_4$ is a substituted alkyl radical, an alkenyl, alkynyl, cycloalkyl radical, a substituted or unsubstituted phenyl or benzyl radical or a 5- to 6-membered heterocyclic radical, and
$R_5$ is an unsubstituted alkyl radical or has the same meaning as $R_4$.

5 Claims, No Drawings

PHENOXYPHENOXYALKANECARBOXYLIC ACID ESTERS

The present invention relates to novel herbicidally active phenoxyphenoxyalkanecarboxylic acid esters, compositions which contain these compounds as active ingredient, and a method of selectively controlling weeds in crops of cultivated plants or of regulating plant growth which comprises the use of these compounds.

The active compounds of the present invention have the formula I

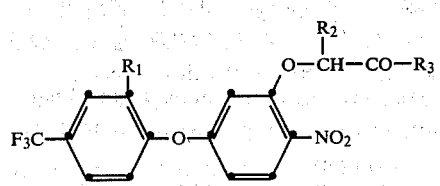
(I)

wherein $R_1$ represents hydrogen, a halogen atom or the cyano group, $R_2$ represents hydrogen or a $C_1$–$C_4$ alkyl group, $R_3$ represents a radical —$OR_4$ or —$SR_5$, $R_4$ represents a $C_1$–$C_{12}$ alkyl radical which is substituted by halogen or cyano or interrupted by one or more oxygen or sulfur atoms, a $C_3$–$C_{12}$ alkenyl, $C_3$–$C_{12}$ alkynyl or $C_3$–$C_{12}$ cycloalkyl radical, a phenyl or benzyl radical which is unsubstituted or mono- or polysubstituted by halogen, $C_1$–$C_4$ alkyl, $C_1$–$C_4$ alkoxy, $C_1$–$C_4$ alkylthio, nitro, cyano or trifluoromethyl, or represents a heterocyclic radical having 5 to 6 members, and $R_5$ represents an unsubstituted $C_1$–$C_{12}$ alkyl radical or has the same meaning as $R_4$.

In formula (I) above, the alkyl, alkenyl or alkynyl radicals can be straight-chain or branched. The preferred halogen atoms are chlorine or bromine atoms. Examples of 5- to 6-membered heterocyclic radicals are furane, pyrane, pyrrole, pyrrolidine, pyridine, piperidine, pyrazole, pyrazolidine, pyrimidine, oxazolidine, oxazole, morpholine, thiazole, thiazolidine etc. These radicals are advantageously bonded through a carbon atom to the oxygen or sulfur atom which links them to the rest of the molecule.

Herbicidally active compounds based on substituted diphenyl ethers are known from various patent specifications. Diphenyl ethers having herbicidal activity are described for example in German Offenlegungsschrift No. 2,311,638 and in Swiss Pat. No. 424,326. These compounds either have an extraordinarily pronounced herbicidal action (German Offenlegungsschrift No. 2,311,638) with less selectivity, or have a one-sided action, for example only against dicotyledonous weeds.

Surprisingly, the active compounds of the formula (I) exhibit not only an excellent action against monocotyledonous and dicotyledonous weeds, but also a marked selectively in barley, wheat and rice, especially in post-emergent application.

The present invention provides a novel group of phenoxyphenoxyalkanecarboxylic acid derivatives which, in low rates of application, are able to influence the growth of plants in a manner which is agriculturally advantageous.

The active compounds of the formula I of the present invention possess a general herbicidal action which is non-specific to grasses, especially in post-emergent application, and they can be used as weed killers in crops of mono- and dicotyledonous plants. They also possess an advantageous growth-regulating action (growth inhibition) and in particular, inhibit the growth of dicotyledonous plants. Exemplary of the useful application of the compounds of the present invention are:

the reduction of the vegetative growth in soya and similar leguminosae, resulting in an increase in the yield of these plants;

the inhibition of the undesirable growth of suckers in tobacco plants, the leading shoots of which have been cut, thus promoting the formation of larger and finer leaves;

the inhibition of the growth of grass and dicotyledonous plants, such as fruit trees, ornamental trees, bushes and hedgerows, with the object of saving cutting work;

the desiccation of plants (cotton, potatoes) before harvesting;

the defoliation of cotton plants before harvesting.

The compounds of the formula I can be subdivided into different groups which comprise those compounds which are most suitable for the respective desired use.

Each of these groups comprises active compounds of similar chemical constitution and having the following formulae:

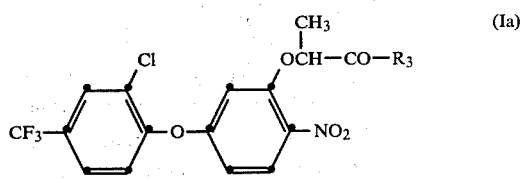
(Ia)

wherein $R_3$ is as defined in formula I.

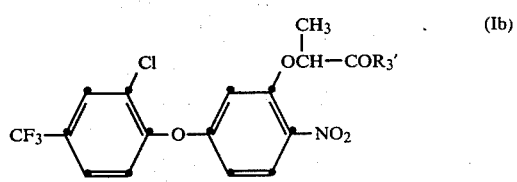
(Ib)

wherein $R_3'$ represents a $C_3$–$C_{12}$ alkenyloxy or alkenylthio radical, a $C_3$–$C_{12}$ alkynyloxy or alkynylthio radical.

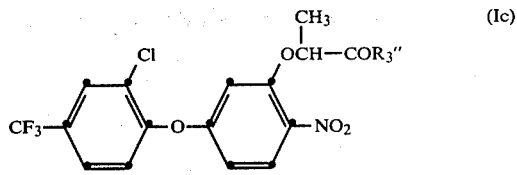
(Ic)

wherein $R_3''$ represents a $C_2$–$C_{12}$ alkoxy or alkylthio radical which is interrupted by one or more oxygen or sulfur atoms.

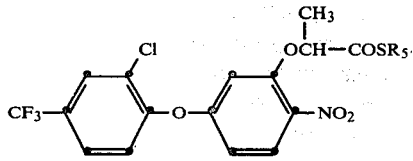

(Id)

wherein R$_5$ is as defined in formula I.

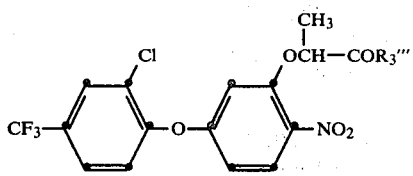

(Ie)

wherein R$_3'''$ represents a phenoxy, phenylthio, benzyloxy or benzylthio radical which is unsubstituted or mono- or polysubstituted by halogen, C$_1$–C$_4$ alkyl, C$_1$–C$_4$ alkoxy, C$_1$–C$_4$ alkylthio, nitro, cyano or trifluoromethyl.

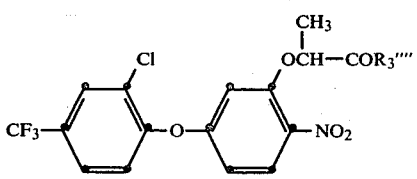

(If)

wherein R$_3''''$ represents a C$_1$–C$_{12}$ alkoxy or alkylthio radical which is substituted by halogen or cyano.

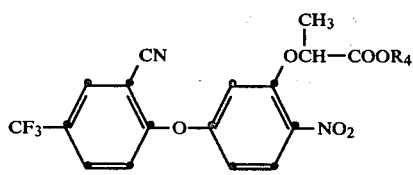

(Ig)

wherein R$_4$ is as defined in formula I.

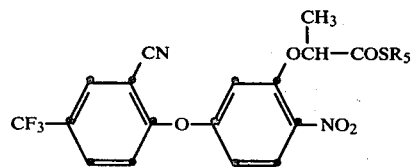

(Ih)

wherein R$_5$ is as defined in formula I.

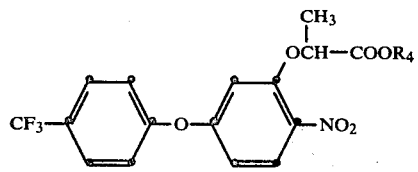

(Ii)

wherein R$_4$ is as defined in formula I.

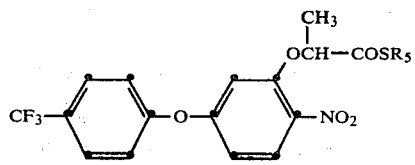

(Ij)

wherein R$_5$ is as defined in formula I.

The phenoxyphenoxyalkanecarboxylic acid derivatives of the present invention have a low toxicity to warm-blooded animals and their application unlikely to cause problems. The suggested rates of application are between 0.1 and 5 kg per hectare.

The compounds of the formula I are obtained by reactions of chemical synthesis which are in themselves known.

A first process consists in nitrating m- (4-trifluoromethylphenoxy)-phenoxycarboxylic acid esters of the formula II

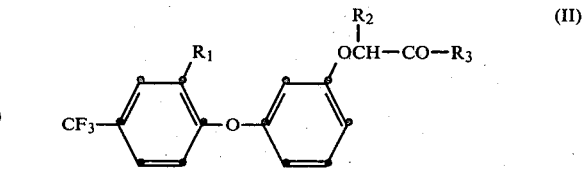

(II)

wherein R$_1$, R$_2$ and R$_3$ are as defined in formula I. The nitration is carried out with nitric acid and sulfuric acid at low temperature (−20° to +20° C.) in an inert organic solvent, for example a chlorinated hydrocarbon. Only a little more than the equimolar amount of nitric acid is used. In this way it is possible to bring the nitro group almost exclusively into the desired ortho-position to the oxycarboxylic acid ester radical.

Provided they are not already known, for example from German Offenlegungsschrift Nos. 2,639,796 or 2,732,442 or from Swiss patent application 9321/76, the starting materials of the formula II can be obtained by condensation of a p-halogenotrifluoromethylbenzene (III) with resorcinol (IV) and subsequent condensation of the resulting m-(trifluoromethylphenoxy)-phenol (V) with an α-halogenocarboxylic acid ester according to the reaction scheme:

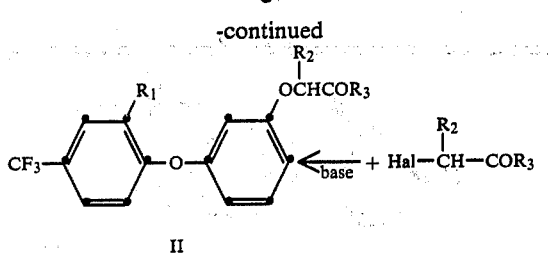

In the formulae II, III, IV and V above, $R_1$, $R_2$ and $R_3$ are as defined in formula I and Hal represents a halogen atom, preferably a chlorine or bromine atom.

In a second process, the compounds of the formula I are obtained by providing the free hydroxyl group in the m-(4-trifluoromethylphenoxy)phenol of the formula V with a protective group, for example by esterification with an acyl halide (acetyl chloride) in the presence of a base, and then nitrating the acetylated diphenyl ether (VI) at low temperature in an inert organic solvent with the equimolar amount of nitric acid in the presence of sulfuric acid. The nitrated and acylated diphenyl ether (VII) is then saponified in a basic medium to the m-hydroxydiphenyl ether (VIII), which in turn can be condensed with an α-halogenocarboxylic acid ester (IX) to provide a m-(4-trifluoromethylphenoxy)-o-nitro-oxycarboxylic acid ester of the formula I.

The sequence of this process can be illustrated by the following reaction scheme:

steps, a temperature range from room temperature to the boiling point of the solvent is indicated.

In certain condensation steps in which a halogen atom is removed or hydrogen halide is formed, the corresponding amount of an acid acceptor should be employed in the reaction.

When the reaction is complete, the final product is isolated, for example by distilling off the solvent and pouring the residue into ice-water.

Suitable solvents for these reactions are in particular organic aprotic solvents or solvent mixtures which dissolve the reactants but do not react with them, for example acetic acid, ethyl acetate, ketones, halogenated hydrocarbons, dimethyl formamide, dimethyl sulfoxide, and also ethers of higher boiling point.

Some of the starting materials are known. Starting materials of these formulae which are not known can be prepared by conventional methods and techniques. Phenoxyphenols can be obtained from resorcinol monoalkyl ether and p-halogenotrifluoromethylbenzene, for example by the methods described in J. Am. Chem. Soc. 61, 2702 (1939) or in Chem. Abst. 54, 922[h] (1960).

The phenoxyphenoxyalkanecarboxylic acid esters of the formula I are also obtained by reacting a phenoxyphenoxyalkanecarboxylic acid halide of the formula X

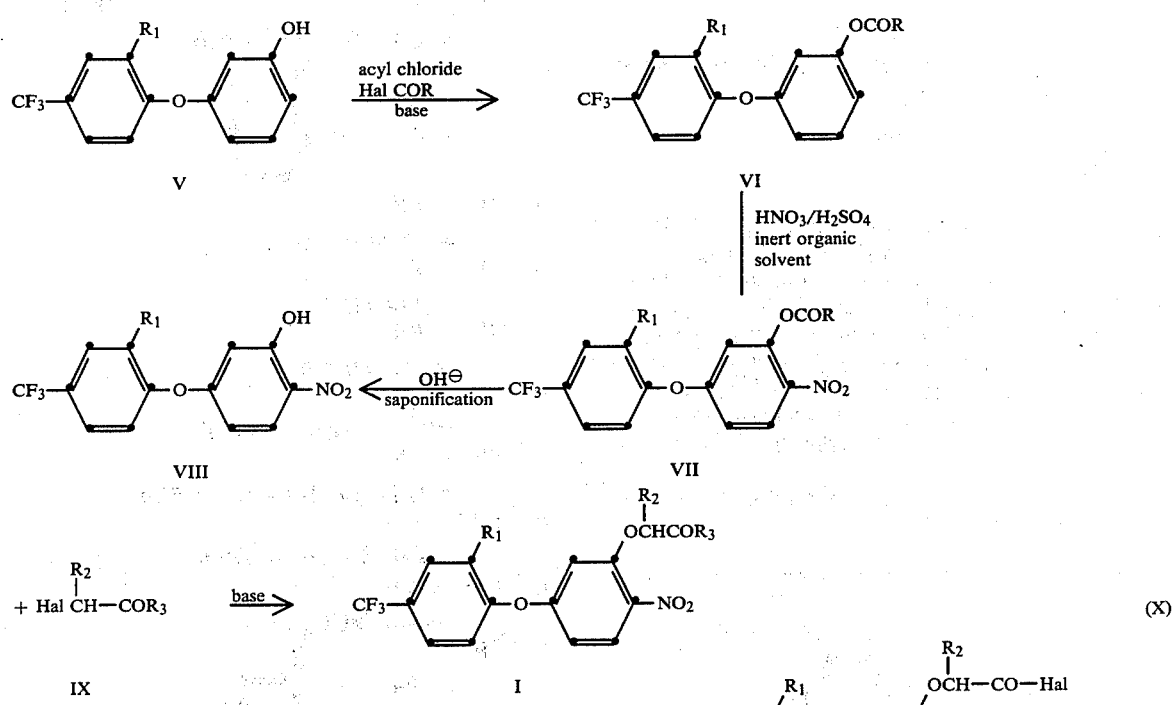

In the above formulae, $R_1$, $R_2$ and $R_3$ are as defined in formula I, Hal represents a halogen atom, preferably a chlorine or bromine atom, and R represents a $C_1$-$C_4$ alkyl radical. The reactants are used in these process steps as far as possible in stoichiometric amounts. The reactions are advantageously carried out in the presence of organic solvents which are inert to the reactants. In the nitration steps, the temperature should be kept as low as possible. In the saponification and condensation

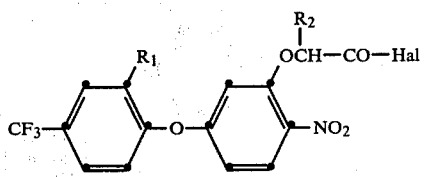

wherein $R_1$ and $R_2$ are as defined in formula I and Hal represents a halogen atom, preferably a chlorine or bromine atom, with an alcohol of the formula $R_4OH$ or with a thiol of the formula

R₅SH wherein R₄ and R₅ are as defined in formula I, in an organic solvent and in the presence of an acid acceptor.

Suitable solvents are almost all organic solvents which dissolve the reactants but do not react with them, for example ethers, ketones, certain stable esters, liquid hydrocarbons, aliphatic, aromatic, and chlorinated hydrocarbons. Preferably trialkylamines are preferably used as acid acceptors, and, provided the solutility enables it, also alkali metal hydroxides, carbonates or ammonia solutions.

The starting materials are best prepared by saponification of an already existing ester of the formula I to the free phenoxyphenoxyalkanecarboxylic acid, which is then reacted with a halogenating agent, such as thionyl chloride, thionyl bromide, phosphoroxy chloride or bromide, phosphorus pentachloride or pentabromide, sulfonyl chloride or bromide, to provide the corresponding acid chloride.

The following Example illustrates the production of a phenoxyphenoxyalkanecarboxylic acid ester of the formula I. Further compounds which are prepared in corresponding manner are listed in the subsequent table. Parts or percentages are by weight.

EXAMPLE

2-[Nitro-5-(2'-chloro-4'-trifluoromethylphenoxy)-phenoxy] propionic acid allyl ester

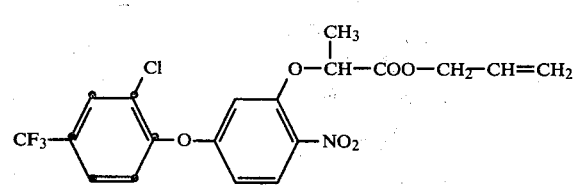

20 g of trimethylamine are added dropwise at 5°–15° C. to a solution of 42.5 g of (α-[2-nitro-3-(2'-chloro-4'-trifluoromethylphenoxy)-phenoxy] propionyl chloride and 12 g of allyl alcohol in 150 ml of toluene. The reaction mixture is stirred overnight at room temperature. Then 50 ml of water are added and the organic phase is separated, dried over sodium sulfate and the solvent is distilled off. Distillation in a high vacuum affords 20.8 g of a viscous oil with a boiling point of 200°–210° C. at 0.04 torr.

The following compounds of the formula I are prepared in analogous manner:

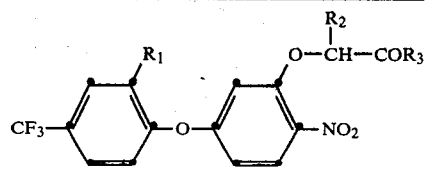

| No. | R₁ | —O—CH(R₂)—COR₃ | physical constant (°C.) |
|---|---|---|---|
| 1 | Cl | —OCH(CH₃)—COOCH₂—CH=CH₂ | b.p. 200°–210°/0.04 torr |
| 2 | Cl | —OCH(CH₃)—COOC₂H₄OCH₃ | b.p. 192°–204°/0.05 torr |
| 3 | Cl | —OCH(CH₃)—COOCH₂—C≡CH | m.p. 74°–76° |
| 4 | Cl | —OCH(CH₄)—COO—(phenyl) | m.p. 119°–121° |
| 5 | Cl | —OCH(CH₃)—COSCH₂—(phenyl) | viscous oil |
| 6 | Cl | —OCH(CH₃)—COSCH₂COOC₂H₅ | viscous oil |
| 7 | Cl | —OCHCOSCH₂—CH=CH₂ | viscous oil |
| 8 | Cl | —OCHCOOC₂H₄OC₂H₄OC₂H₅ | viscous oil |
| 9 | H | —OCH(CH₃)—COO—CH₂—C≡CH | viscous oil |
| 10 | H | —OCH(CH₃)—COO—(CH₃-phenyl) | |
| 11 | H | —OCH(CH₃)—COOC₂H₄OCH₃ | |
| 12 | H | —OCH(CH₃)—COOH | |
| 13 | H | —OCH(CH₃)—COSC₂H₅ | |
| 14 | H | —OCH(CH₃)—COSCH₂—CH=CH₂ | |
| 15 | CN | —OCH(CH₃)—COOCH₂—CH₂—CH=CH₂ | |
| 16 | CN | —OCH(CH₃)—COOCH₂—CH=CH | |
| 17 | CN | —OCH(CH₃)—COOC₂H₄OCH₃ | |
| 18 | CN | —OCH(CH₃)—COO—(CH₃-phenyl-NO₂) | |
| 19 | CN | —OCH(CH₃)—COSCH₃ | |
| 20 | CN | —OCH(CH₃)—COSC₂H₅ | |
| 21 | CN | —OCH(CH₃)—COSCH₂—CH=CH₂ | |

-continued

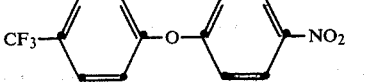

| No. | R₁ | $-O-\underset{\underset{R_2}{|}}{C}H-COR_3$ | physical constant (°C.) |
|---|---|---|---|
| 22 | Cl | $-O\underset{\underset{CH_3}{|}}{C}H-COO-$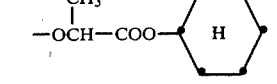H | b.p. 230°0.001 torr |
| 23 | Cl | $-O\underset{\underset{CH_2}{|}}{C}H-COOH$ | viscous oil |
| 24 | Cl | $-O\underset{\underset{CH_3}{|}}{C}H-COO-$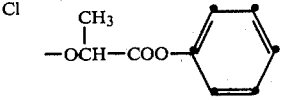 | m.p. 64°-67° |
| 25 | Cl | $-O\underset{\underset{CH_3}{|}}{C}H-COOC_2H_4SCH_3$ | viscous oil |
| 26 | Cl | $-O\underset{\underset{CH_3}{|}}{C}H-COOCH_2-$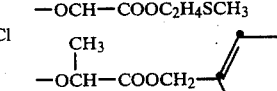 | viscous oil |
| 27 | H | $-O\underset{\underset{CH_3}{|}}{C}H-COOCH_2C\equiv CH$ | |
| 28 | H | $-O\underset{\underset{CH_3}{|}}{C}H-COOC_2H_4OC_2H_5$ | |
| 29 | CN | $-O\underset{\underset{CH_3}{|}}{C}H-COOCH_2CH=CH_2$ | |
| 30 | CN | $-O\underset{\underset{CH_3}{|}}{C}H-COOC_2H_4OC_2H_4OC_2H_5$ | |
| 31 | Cl | $-O\underset{\underset{CH_3}{|}}{C}H-COOC_2H_4Cl$ | viscous oil |
| 32 | Cl | $-O\underset{\underset{CH_3}{|}}{C}H-COOC_2H_4CN$ | viscous oil |

The invention also relates to herbicidal and plant growth-regulating compositions which contain a novel active compound of the formula I, as well as to a method of controlling weeds by pre- and post-emergent application and of inhibiting the growth of mono- and dicotyledonous plants, especially grasses, cereals, soya and tobacco shoots.

The compositions of the present invention can be in the conventional formulations.

The compositions of the present invention are obtained in known manner by homogeneously mixing and grinding active substances (compounds) of the formula I with suitable carriers, with or without the addition of dispersants or solvents which are inert to the active substances. The active substances can be processed to the following formulations:
solid formulations:
  dusts, tracking powders, granules (coated granules, impregnated granules and homogeneous granules);
active substance concentrates which are dispersible in water:
  wettable powders, pastes, emulsions;
liquid formulations:
  solutions.

The concentration of active substance in the above described compositions is between 0.1 and 95%, preferably between 1 and 80%. Formulations can be diluted to concentrations as low as 0.001%. The rates of application are ordinarily from 0.1 to 10 kg, preferably from 0.25 to 5 kg, of active substance per hectare. The active substances of the formula I can be formulated for example as follows (parts are by weight):

Emulsifiable Concentrate

The following ingredients are mixed to manufacture a 25% emulsifiable concentrate:
  25 parts of 2-[2-nitro-5-(2'-chloro-4'-trifluoromethylphenoxy)-phenoxy] propionic acid allyl ester,
  5 parts of a mixture of nonylphenolpolyoxyethoxyethylene and calcium dodecylenesulfonate,
  15 parts of cyclohexanone,
  55 parts of xylene.
This concentrate can be diluted with water to give emulsions of suitable concentrations.

Dusts: The following substances are used to prepare (a) a 5% dust and (b) a 2% dust:
  (a) 5 parts of 2-[2-nitro-5-(2'-chloro-4'-trifluoromethylphenoxy)-phenoxy] propionic acid allyl ester,
  95 parts of talc;
  (b) 2 parts of the above active substance
  1 part of highly dispersed silicic acid
  97 parts of talc.
The active substances are mixed with the carriers and ground.

Granulate: The following substances are used to prepare a 5% granulate:
  5 parts of the above active substance
  0.25 part of epichlorohydrin
  0.25 part of cetyl polyglycol ether with 8 moles of ethylene oxide,
  3.25 parts of polyethylene glycol
  91 parts of kaolin (particle size 0.3–0.8 mm).
The active substance is mixed with epichlorohydrin and the mixture is dissolved in 6 parts of acetone. Then polyethylene glycol and cetyl polyglycol ether are added. The resulting solution is sprayed on kaolin and subsequently evaporated in vacuo.

Wettable Powders

The following constituents are used to prepare (a) a 50%, (b) a 25% and (c) a 10% wettable powder:
(a)
  50 parts of 2-[2-nitro-5-(4'-trifluoromethylphenoxy)-phenoxy] propionic acid allyl ester,
  5 parts of sodium dibutylnaphthylsulfonate,
  3 parts of naphthalenesulfonic acid/phenolsulphonic acid/formaldehyde condensate (3:2:1),
  20 parts of kaolin,
  22 parts of Champagne chalk;
(b)
  25 parts of the above active substance,
  5 parts of sodium oleylmethyltauride,
  2.5 parts of naphthalenesulfonic acid/formaldehyde condensate,
  0.5 part of carboxymethyl cellulose,
  5 parts of neutral potassium aluminium silicate,
  62 parts of kaolin;
(c)
  10 parts of the above active substance,
  3 parts of a mixture of the sodium salts of saturated fatty alcohol sulfates, 5 parts of naphthalenesulfonic acid/formaldehyde condensate,
82 parts of kaolin.

The indicated active substance is applied to the corresponding carriers (kaolin and chalk) and then these are mixed and ground, to yield wettable powders of excellent wettability and suspension power. By diluting these wettable powders with water it is possible to obtain suspension having the desired concentration of active substance.

Paste

The following substances are used to prepare a 45% paste:
45 parts of 2-[2-nitro-5-(4'-trifluoromethylphenoxy)-phenoxy] propionic acid allyl ester,
5 parts of sodium aluminium silicate,
14 parts of cetyl polyglycol ether with 8 moles of ethylene oxide,
1 part of oleyl polyglycol ether with 5 moles of ethylene oxide,
2 parts of spindle oil,
10 parts of polyethylene glycol,
23 parts of water.

The active substance is homogeneously mixed with the adjuvants in appropriate devices and ground, yielding a paste from which, by dilution with water, it is possible to obtain suspensions of the desired concentration of active substance. Instead of using the respective active substance indicated in the foregoing formulation examples, it is also possible to use another of the compounds comprised by the formula I.

The active substances contained in the compositions of the present invention influence the plant growth in different ways. Thus they inhibit, delay or prevent primarily the growth and germination. Their action is consequently both a pre- and post-emergent herbicidal and growth-inhibiting action.

The novel active substances of the formula I have a good action against monocotyledonous and dicotyledonous weeds as well as a pronounced selectivity in barley, wheat and rice, especially in post-emergent application.

The following test methods were employed to establish the usefulness of the compounds of the formula I as pre- and post-emergent herbicides.

Preemergent herbicidal action (germination inhibition)

In a greenhouse, immediately after sowing the test plants in seed dishes the surface of the soil is treated with an aqueous suspension of the active substances obtained from a 25% wettable powder. Different concentration series were used, corresponding to 4 to 2 kg of active substance per hectare respectively. The seed dishes are kept in the greenhouse at 22°–25° C. and 50 to 70% relative humidity. The test is evaluated 3 weeks later according to the following rating:

| | | |
|---|---|---|
| 1 | = | plants have not germinated or are totally withered |
| 2–8 | = | intermediate stages of damage |
| 9 | = | plants undamaged (as untreated control). |

Post-emergent herbicidal action (Contract herbicide)

A large number (at least 7) of weeds and cultivated plants, both mono- and dicotyledonous, were sprayed after emergence in the 4- to 6-leaf stage with an aqueous active substance emulsion in rates of 0.5 and 1 kg of active substance per hectare and kept at 24°–26° C. and 45–60% relative humidity. The test was evaluated, as in the preemergent test, 15 days after treatment in accordance with the same rating.

Pre-emergent

| rate of application in kg/ha | Compound No. 1 | | 2 | | A | |
|---|---|---|---|---|---|---|
| | 4 | 2 | 4 | 2 | 4 | 2 |
| Plant | | | | | | |
| barley | 5 | 7 | 6 | 8 | 1 | 1 |
| wheat | 9 | 9 | 9 | 9 | 1 | 1 |
| maize | 6 | 8 | 2 | 4 | 2 | 2 |
| avena fatua | 2 | 3 | 6 | 8 | 1 | 1 |
| lolium perenne | 5 | 5 | 6 | 9 | 1 | 1 |
| alopecurus myos. | 1 | 1 | 3 | 6 | 1 | 1 |
| cyperus esc. | 2 | 4 | 2 | 3 | 4 | 9 |
| rottboellia exalt. | 2 | 5 | 3 | 7 | 1 | 1 |
| digitaria sang. | 1 | 1 | 1 | 1 | 1 | 1 |
| setaria italica | 1 | 1 | 1 | 1 | 1 | 1 |
| echinochloa c.g. | 1 | 1 | 1 | 2 | 1 | 1 |
| sida spinosa | 1 | 1 | 1 | 1 | 1 | 1 |
| sesbania exaltata | 1 | 1 | 1 | 4 | 1 | 1 |
| amaranthus retrof. | 1 | 1 | 1 | 1 | 1 | 1 |
| sinapis alba | 1 | 1 | 1 | 1 | 1 | 3 |
| ipomoea purp. | 1 | 1 | 1 | 1 | 1 | 1 |
| galium aparine | 1 | 1 | 1 | 1 | 1 | 1 |
| pastinaca sativa | 1 | 1 | 1 | 1 | 1 | 1 |
| rumex sp. | 1 | 1 | 1 | 1 | 1 | 1 |
| chrysanthemum l. | 1 | 1 | 1 | 1 | 1 | 1 |
| abutilon sp. | 1 | 1 | 1 | 1 | 1 | 1 |
| solanum nigrum | 1 | 1 | 1 | 1 | 1 | 1 |

A = 2-chloro-4-trifluoromethyl-3'-ethoxy-4'-nitro-diphenyl ether, known from German Offenlegungsschrift 2 311 638 (Compound 3 Z.)

Post-emergent

| kg/ha | Compound No. 1 | | 2 | | A | |
|---|---|---|---|---|---|---|
| | 1 | 0.5 | 1 | 0.5 | 1 | 0.5 |
| Plant | | | | | | |
| barley | 6 | 7 | 4 | 7 | 1 | 1 |
| wheat | 7 | 8 | 6 | 8 | 2 | 2 |
| rice | 6 | 8 | 3 | 8 | 1 | 1 |
| avena fatua | 6 | 7 | 3 | 7 | 1 | 1 |
| lolium perenne | 2 | 2 | 3 | 6 | 1 | 1 |
| alopecurus myos. | 2 | 4 | 2 | 2 | 1 | 1 |
| cyperus esc. | 5 | 9 | 3 | 3 | 3 | 3 |
| rottboellia exalt. | 3 | 4 | 2 | 4 | 1 | 2 |
| digitaria sang. | 1 | 2 | 1 | 2 | 1 | 1 |
| sectaria italica | 1 | 2 | 1 | 1 | 1 | 1 |
| echinochloa c.g. | 1 | 1 | 1 | 2 | 1 | 1 |
| sida spinosa | 1 | 1 | 1 | 2 | 2 | 2 |
| sesbania exalt. | 1 | 1 | 1 | 1 | 1 | 1 |
| amaranthus retro. | 1 | 1 | 1 | 1 | 1 | 1 |
| sinapis alba | 1 | 1 | 1 | 1 | 1 | 1 |
| impomoea purp. | 1 | 1 | 1 | 1 | 1 | 1 |
| galium aparine | 2 | 2 | 1 | 1 | 1 | 1 |
| pastinaca sativa | 1 | 1 | 1 | 1 | 1 | 1 |
| chrysanthemum leuc. | 1 | 1 | 1 | 1 | 4 | 4 |
| abutilon sp. | 1 | 1 | 1 | 1 | 1 | 1 |
| solanum nigrum | 1 | 1 | 1 | 1 | 1 | 1 |
| matricaria cham. | 1 | 1 | 1 | 1 | 2 | 2 |

The compounds of the formula I also possess advantageous growth-regulating effects. They are suitable for the defoliation and desiccation of non-lignified parts of plants above the soil, in particular for the defoliation and desiccation of cotton plants, leguminosae, sorghum, potatoes and vines before harvesting. This action was testet as follows:

Defoliation and desiccation

Cotton plants of the variety "Delta Pine" are reared in a greenhouse. After blossoming, they are sprayed with an active substances suspension in amounts corresponding to a field rate of application of 1.2, 0.6 and 0.3 kg per hectare. The plants are then left in the greenhouse and the test is evaluated 15 days after treatment.

Defoliation: The leaves are counted before treatment and when evaluating the test. The loss is noted and expressed in accordance with the rating below.

Desiccation: The leaves remaining on the plant are examined for their degree of desiccation and the result is likewise rated as indicated below:

9 = 0–11% defoliation or desiccation
8 = 11–22% defoliation or desiccation
7 = 23–33% defoliation or desiccation
2 = 78–88% defoliation or desiccation
1 = 89–100% defoliation or desiccation

| Compound rate of application in kg/ha | Defoliation | | (Desiccation) |
|---|---|---|---|
| | 1.2 | 0.6 | 0.3 |
| No. 1 | 1(1) | 1(1) | 1(1) |
| No. 2 | 2(1) | 2(1) | 3(1) |
| B | 4(1) | 7(2) | 7(3) |

What is claimed is:
1. 2-[2-Nitro-5-(2'-chloro-4'-trifluoromethylphenoxy)-phenoxy] propionic acid methoxyethyl ester.
2. A herbicidal and plant growth-regulating composition which contains as active ingredient an effective amount of the compound of claim 1, together with the inert adjuvants conventionally employed therein.
3. A method of selectively controlling weeds in crops of cultivated plants which comprises applying thereto a herbicidally effective amount of the compound of claim 1.
4. A method of regulating plant growth which comprises applying to said plants an effective growth regulating amount of the compound of claim 1.
5. A method of desiccating and defoliating cotton and potatoes shortly before harvesting, which comprises applying thereto an effective desiccating and defoliating amount of the compound of claim 1.

* * * * *